United States Patent
Euzen et al.

(10) Patent No.: US 6,908,878 B2
(45) Date of Patent: Jun. 21, 2005

(54) CATALYST COMPOUND FOR THE METATHESIS OF OLEFINS

(75) Inventors: Patrick Euzen, Paris (FR); Séverine Guibert, Bougival (FR); Virginie Kruger-Tissot, Malakoff (FR); Georges Vidouta, Aubergenville (FR)

(73) Assignee: Institut Francais du Petrole, Rueil-Malmaison Cedex (FR)

( * ) Notice: Subject to any disclaimer, the term of this patent is extended or adjusted under 35 U.S.C. 154(b) by 121 days.

(21) Appl. No.: 10/189,328

(22) Filed: Jul. 5, 2002

(65) Prior Publication Data

US 2003/0023125 A1 Jan. 30, 2003

(30) Foreign Application Priority Data

Jul. 4, 2001 (FR) .............................................. 01 08911

(51) Int. Cl.⁷ ................................................ B01J 21/00
(52) U.S. Cl. ........................ 502/241; 502/254; 502/255
(58) Field of Search ................................ 502/241, 254, 502/255

(56) References Cited

U.S. PATENT DOCUMENTS

| | | | | |
|---|---|---|---|---|
| 4,567,159 A | * | 1/1986 | Banks et al. ................. | 502/219 |
| 5,114,899 A | | 5/1992 | Lin | |
| 5,753,721 A | * | 5/1998 | Hafner et al. ................. | 522/53 |
| 5,776,997 A | * | 7/1998 | Hafner et al. ................. | 522/65 |
| 5,854,299 A | * | 12/1998 | Muhlebach et al. .......... | 522/66 |
| 5,883,272 A | * | 3/1999 | Noweck et al. ............. | 554/163 |
| 6,093,779 A | * | 7/2000 | Van Der Schaaf et al. . | 526/285 |
| 6,683,019 B2 | * | 1/2004 | Gartside et al. ............ | 502/241 |
| 2003/0045765 A1 | * | 3/2003 | Basset et al. ............... | 585/700 |
| 2003/0166461 A1 | * | 9/2003 | Angeletakis et al. ........ | 502/159 |

FOREIGN PATENT DOCUMENTS

| | | |
|---|---|---|
| EP | 0363537 | 4/1990 |
| WO | 9529755 | 11/1995 |

* cited by examiner

*Primary Examiner*—Steven Bos
(74) *Attorney, Agent, or Firm*—Millen, White, Zelano, Branigan, P.C.

(57) ABSTRACT

An improved catalyst composition for the metathesis of olefins comprises at least one porous mineral carrier based on alumina, at least one compound of rhenium, molybdenum, or tungsten, and further includes silicon in an oxide form.

30 Claims, No Drawings

CATALYST COMPOUND FOR THE METATHESIS OF OLEFINS

FIELD OF THE INVENTION

This invention relates to a catalyst based on rhenium, molybdenum, or tungsten, comprising a porous carrier based on alumina, as well as a silicon compound. It also relates to a process for preparing said catalyst as well as its use in the metathesis of olefins.

DESCRIPTION OF RELATED PRIOR ART

The metathesis of olefins, i.e., the reaction of mutual redistribution of alkylidene groups, holds great practical potential, for example for the mutual rebalancing of light olefins resulting from steam cracking, such as ethylene, propylene, and the butenes.

Different types of catalysts are suitable for use in the metathesis reaction, whether homogeneous, if their constituent elements are all soluble in the reaction environment, or heterogeneous, if at least one of the elements is insoluble in said environment. These catalysts are most often based on rhenium, molybdenum, or tungsten. The heterogeneous catalysts are particularly suitable if the active metal is expensive and if it is necessary to provide for its recovery without losses and its reuse. This is the case, for example, with catalysts based on rhenium, whose use in the heterogeneous form was recommended to catalyze the metathesis of simple olefins (U.S. Pat. Nos. 3,641,189 and 3,676,520).

These catalysts can be prepared by the conventional methods of heterogeneous catalysis, on a porous carrier consisting of a refractory oxide, having an acid, neutral, or basic character, such as the oxide of aluminum, silicon, magnesium, or titanium (U.S. Pat. No. 3,642,931). Among the various carriers, alumina or a carrier containing alumina would seem to offer the most useful properties for giving the catalyst good activity and good stability.

Numerous modifications to base catalysts consisting of rhenium, molybdenum, or tungsten, on a porous carrier consisting of a refractory oxide, have been described to improve its properties. Thus beneficial effects were found by adding alkaline or earth-alkaline compounds (U.S. Pat. Nos. 3,594,440 and 3,637,892), acidic anions (U.S. Pat. No. 3,697,613), tin oxides (British Patent Application No. 1,377, 161), boron oxide (U.S. Pat. No. 5,055,628), aluminum compounds (U.S. Pat. No. 5,898,092), rare earth elements (U.S. Pat. No. 3,728,414) or organometallic compounds, for example tin, lead (J. C. Mol, C. Boelhouwer et al., J. Chem. Soc. Chem. Comm., (1977), 198) or aluminum (U.S. Pat. No. 5,898,092).

SUMMARY OF THE INVENTION

This invention relates to an improved composition for a metathesis catalyst, characterized in that it comprises at least one porous mineral carrier selected from among the aluminas and the silica-aluminas, containing at least 75% by weight of alumina, at least one compound of rhenium, molybdenum, or tungsten, and in that it further includes silicon in an oxide form.

It was in fact surprisingly found that the addition of silicon in an oxide form to these carriers or to the catalysts clearly improves their activity. This then allows the use of lower proportions of metal for identical activity.

DETAILED DESCRIPTION OF THE INVENTION

The porous mineral carrier consists more precisely of an alumina or a silica-alumina having a specific surface of 10 to 400 $m^2/g$, and preferably at least 50 $m^2/g$, and a sufficient pore volume, for example at least 0.1 ml/g, and preferably 0.3–1 ml/g. For example, an alumina of the same type as those of the catalysts for catalytic reforming can be used.

More precisely, the catalytic compounds of the invention comprise at least three constituents:
 at least one porous mineral carrier as defined above;
 a proportion of 0.01 to 20% by weight of rhenium, molybdenum, or tungsten in an oxide form;
 and a proportion of 0.01 to 10% by weight of silicon in an oxide form.

The catalysts according to the invention can be prepared according to methods known to one skilled in the art. More precisely, the preparation process according to the invention comprises the following steps:
 (a) a step in which a rhenium, molybdenum, or tungsten compound is placed on the porous mineral carrier;
 (b) a step in which drying is performed at a temperature of 0 to 250° C.;
 (c) an optional step in which thermal activation is performed by calcination at a temperature of 250° C. to 1000° C.;
 (d) a step in which the solid resulting from steps (a) to (c) is impregnated with a solution containing silicon;
 (e) an optional step in which drying is performed at a temperature of 0 to 250° C.; and
 (f) a step in which thermal activation is performed by calcination at a temperature of 250° C. to 1000° C.

The calcination steps are performed in an oxidizing atmosphere, for example in air.

The precursor of the rhenium, molybdenum, or tungsten compound used for step (a) is preferably one of rhenium heptoxide, ammonium perrhenate, perrhenic acid, ammonium molybdate and ammonium tungstate. The rhenium, molybdenum, or tungsten compound can be placed on the carrier by any method known to one skilled in the art, for example by sublimation in vapor phase, by impregnation in solution or by dry impregnation. In this last method, which is preferred the rhenium, molybdenum, or tungsten compound is placed in solution in water or in an organic solvent, for example a hydrocarbon, an alcohol, or an ether. The quantity of metal on the carrier is controlled by selecting the concentration of the impregnation solution, its quantity being such that the volume of this solution is equal to or slightly less than the pore volume of the solid to be impregnated. When the quantity of the metal that is desired to be impregnated is greater than that which allows the introduction of a solution at its saturation limit, the procedure must be performed several times, with dryings in between to eliminate the impregnation solvent, at a temperature, for example, from 90 to 250° C., preferably 100 to 180° C. This makes it possible to introduce 0.01 to 20%, preferably 0.1 to 15%, and yet more advantageously 0.5 to 10% by weight of metal.

After placing the rhenium, molybdenum, or tungsten precursor on the carrier, drying (step (b)) is performed at a temperature, for example, of 90 to 250° C., preferably 100 to 180° C., then an optional calcination (step (c)) at a temperature, for example, of 250 to 1000° C., for a period of 10 minutes to 10 hours. After drying and optional calcination, the solid is recooled in a dry, inert atmosphere, for example in nitrogen or argon.

In the step where silicon is introduced, various silicon sources can be used consisting in general of compounds containing Si—O bonds. We mention, for example, ethyl orthosilicate, siloxanes, and silicic acid. Silicon can thus be added by impregnation of an alcoholic solution of ethyl orthosilicate or by impregnation of a compound corresponding to the general formula: $R^1[R^3R^4SiO]_nR^2$. In this formula, $R^i$ (i=1, 2, 3, or 4) can be one of the following groups: R, OR, COOR, or $SiR^5R^6R^7$, with $R^5$, $R^6$, and $R^7$, identical or different, where R, $R^5$, $R^6$, and $R^7$ are each a hydrocarbyl radical containing 1 to 20 carbon atoms, for example alkyl, cycloalkyl, alkenyl, aryl, substituted aryl, or substituted cycloalkyl, this radical being able to be substituted by at least one alkoxy group or at least one halogen and n is a whole number between 1 and 100.

This compound can be placed on the catalyst by all methods known to one skilled in the art.

A preferred method is to proceed by dry impregnation of an aqueous solution containing a silicon compound of the silicone type such as, for example, Rhodorsil EP1® sold by the firm PROLABO. Then the silicon concentration of the solution is adjusted depending on the quantity of silicon that is desired to be deposited on the solid, so that the volume of this solution is equal to or slightly less than the pore volume of the solid to be impregnated. This makes it possible to introduce 0.01 to 10%, preferably 0.05 to 5% by weight of silicon (expressed as silicon metal).

After introducing the promoter compound, the preparation of the catalyst can be ended by an optional drying (step (c)), in a vacuum or in a preferably inert gas stream, at a temperature of 0 to 250° C. Step (f) of thermal activation by calcination at a temperature of 250 to 1000° C. is then necessary to activate the catalyst.

Steps (d), (e), and (f) can thus advantageously take place in situ in the metathesis reactor, before the reaction, or even ex situ and the modified catalyst is loaded directly into the reactor for the reaction.

In another method for catalyst preparation, steps (a) and (d) can be reversed. Then there is performed:

(a) a step in which a solution containing silicon is impregnated on a porous mineral carrier;

(b) a step of drying at a temperature of 0 to 250° C.;

(c) an optional step of thermal activation by calcination in an oxidizing atmosphere at a temperature of 250° C. to 1000° C.;

(d) a step in which a rhenium, molybdenum, or tungsten compound is placed on the solid resulting from steps (a) to (c);

(e) an optional drying step at a temperature of 0 to 250° C.;

(f) a step of thermal activation by calcination at a temperature or 250° C. to 1000° C.

The preparation process according to the invention is particularly advantageous in the case of catalysts based on rhenium. In this case, any existing carrier laden with rhenium oxide can be used and the following steps performed:

(d) a step in which a solution containing silicon is impregnated onto a carrier laden with rhenium oxide;

(e) an optional step of drying at a temperature of 0 to 250° C.; and (f) a step of thermal activation by calcination at a temperature of 250° C. to 1000° C.

In this case, currently commercially available catalysts based on rhenium are suitable.

The invention also has as its object a process of metathesis of olefins in the presence of the catalyst defined above, at a temperature of 0 to +500° C., preferably 20 to +150° C. in the case of catalysts based on rhenium. The metathesis reaction is performed in gaseous or liquid phase. The reaction can be performed in batch, in a shaken reactor, or continuously, by making the reagents pass through a fixed bed, a mobile bed, or a fluidized bed, of the catalyst.

The pressure at which the reaction is performed is not critical. For a liquid phase procedure, however, it is necessary to maintain a pressure at least equal to the vapor pressure of the reaction mixture at the temperature of the reaction.

The metathesis reaction is performed preferably in the absence of solvent. The presence of a solvent such as a hydrocarbon, however, or a halogenated, aliphatic, cyclanic, or aromatic hydrocarbon is not harmful.

The olefins capable of reacting in metathesis in the presence of the carried catalyst based on rhenium described above can be linear olefins corresponding to the general formula: $R^8R^9C=CR^{10}R^{11}$, where $R^8$, $R^9$, $R^{10}$ and $R^{11}$, identical or different, are hydrogen or a hydrocarbyl radical of 1 to 20 carbon atoms. The olefins can also have a cyclic structure, the cycle comprising 3 to 20 carbon atoms. An olefin can be made to react on itself, or several olefins can be made to react among themselves in a mixture. An example of an application is the production of propylene by reaction of ethylene with the 2-butenes, or the inverse transformation reaction of propylene in a mixture of ethylene and butenes-2. Other olefins capable of reacting in metathesis are the monoolefins or the polyolefins, linear or cyclic, carrying functional groups such as, for example, halogens or ester groups. The process can also use, in co-metathesis, a mixture of the preceding olefins.

The following examples illustrate the invention without limiting its scope.

EXAMPLE 1

Preparation of the Catalyst 9.27 g of a cubic gamma alumina having a specific surface of 184 m²/g and a pore volume of 0.67 ml/g is calcined at 500° C. in air. A solution for dry impregnation of rhenium is prepared by diluting 0.46 ml of a concentrated aqueous solution of perrhenic acid containing 54.08% by weight of rhenium (specific mass: 2.417 g/ml) in 5 ml of water. This solution is impregnated onto the previously calcined solid. After 30 minutes of contact at ambient temperature, the solid obtained is dried in an oven at 120° C. during one night. It is then calcined in an air stream (about 20 l/h) dried by passing through a molecular sieve bed, at a temperature of 550° C. for 2 hours. During the final cooling period, a stream of dry nitrogen is substituted for the air stream. Then an aqueous emulsion of 0.4 g of Rhodorsil EP1® (containing 13% by weight of silicon) in 5 ml of water is prepared. This solution is impregnated onto the previously calcined solid. After 1 hour of contact at ambient temperature, the solid obtained is dried in an oven at 120° C. for one night. Then it is calcined in an air stream (about 20 l/h) dried by passing through a molecular sieve bed, at a temperature of 550° C. for 2 hours. During the final cooling period, a stream of dry nitrogen is substituted for the air stream. The solid obtained is stored and handled in a dry nitrogen atmosphere. It rhenium content is 6% by weight and its silicon content is 0.5% by weight.

Use in Metathesis

In a reactor consisting of a stainless steel tube provided with a double jacket with water circulation making it possible to regulate the temperature, the catalyst prepared above is loaded under the protection of air and humidity. Liquid propylene is injected by a pump at the base of the reactor, with a throughput of 46 g/h. The temperature is adjusted to 35° C. and the pressure is kept at 3.5 MPa using a regulator placed downstream from the reactor. Under these conditions, the initial conversion of propylene at the reactor discharge is 33%, in an equimolar mixture of ethylene and butenes-2.

EXAMPLE 2

A new batch of catalyst is prepared as in example 1, except that the steps for impregnating rhenium and silicon are reversed, A catalyst containing 0.5% by weight of silicon and 6% by weight of metallic rhenium is obtained and it is stored in an inert, dry atmosphere before use.

Use in Metathesis 10 g of the catalyst prepared above is loaded into the same apparatus as described in example 1. Liquid propylene is injected using a pump at the base of the reactor, with a throughput of 46 g/h. The temperature is adjusted to 35° C. and the pressure is maintained at 3.5 MPa by a regulator placed downstream from the reactor. Under these conditions, the initial conversion of propylene at the reactor discharge is 27%, in an equimolar mixture of ethylene and butenes-2.

EXAMPLE 3

A new batch of catalyst is prepared as in example 1 starting with 10 g of alumina, except that the step of impregnation with silicon is performed with 0.38 g of ethyl orthosilicate in 5 ml of ethanol. The rhenium impregnation step, as well as the drying and calcination phase, are identical to those described in example 1. A catalyst is obtained that contains 6% by weight of metallic rhenium and 0.5% by weight of silicon and it is stored in an inert, dry atmosphere before use.

Use in Metathesis 10 g of the catalyst prepared above is loaded into the same apparatus as described in example 1. Liquid propylene is injected using a pump at the base of the reactor, with a throughput of 46 g/h. The temperature is adjusted to 35° C. and the pressure is maintained at 3.5 MPa by a regulator placed downstream from the reactor. Under these conditions, the initial conversion of the propylene at the reactor discharge is, 24%, in an equimolar mixture of ethylene and butenes-2.

EXAMPLE 4 (COMPARATIVE)

A new batch of catalyst is prepared as in example 1, except that the silicon impregnation step and the following steps are omitted. The rhenium impregnation step as well as the drying and calcination phase are identical to those described in example 1. A catalyst that contains 6% by weight of metallic rhenium is obtained and it is stored in an inert, dry atmosphere before use.

Use in Metathesis 10 g of the catalyst prepared above is loaded into the same apparatus as described in example 1. Liquid propylene is injected using a pump at the base of the reactor, with a throughput of 46 g/h. The temperature is adjusted to 35° C. and the pressure is maintained at 3.5 MPa using a regulator placed downstream from the reactor. Under these conditions, the initial conversion of propylene at the reactor discharge is 19%, in an equimolar mixture of ethylene and butenes-2.

This comparative example illustrates the progress brought by the presence of silicon regarding the activity of the catalyst.

EXAMPLE 5 (COMPARATIVE)

A new batch of catalyst is prepared as in example 1. The carrier used in this example is a commercial siliceous alumina containing 0.7% by weight of silicon. The rhenium impregnation step, as well as the drying and calcination phase, are identical to those described in example 1, the silicon impregnation step and the following steps are omitted. A catalyst containing 6% by weight of metallic rhenium and 0.65% by weight of silicon coming from the carrier is obtained and is stored in an inert, dry atmosphere before use.

Use in Metathesis 10 g of the catalyst prepared above is loaded into the same apparatus as described in example 1. Liquid propylene is injected using a pump at the base of the reactor, with a throughput of 46 g/h. The temperature is adjusted to 35° C. and the pressure is kept at 3.5 MPa by a regulator placed downstream from the reactor. Under these conditions, the initial conversion of propylene at the reactor discharge is 20%, in an equimolar mixture of ethylene and butenes-2.

This comparative example illustrates the progress brought by the presence of silicon added onto the catalyst regarding the activity of the catalyst, compared to the presence of silicon coming from the carrier.

The entire disclosure[s] of all applications, patents and publications, cited herein and of corresponding French Application No. 01/08.911, filed Jul. 4, 2001 is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A catalyst composition comprising at least one porous mineral carrier selected from among aluminas and silica-aluminas containing at least 75% by weight of alumina, said composition further comprising on said carrier
   at least one rhenium compound, and a silicon compound containing silicon in oxide form introduced onto the carrier in the form of an organic silicon compound.

2. A catalyst composition according to claim 1, wherein said composition comprises:
   0.01 to 20% by weight of rhenium in oxide form; and
   0.01 to 10% by weight of silicon.

3. A catalyst composition according to claim 1, wherein the porous mineral carrier has a surface of 10 to 400 m$^2$/g and a pore volume of at least 0.1 ml/g.

4. A catalyst composition according to claim 1, comprising rhenium in oxide form.

5. A catalyst composition according to claim 1, wherein the silicon compound is introduced in the form of a compound with Si—O bonds selected from the group consisting of ethyl tetraorthosilicate and compounds of general formula $R^1[R^3R^4SiO]_nR^2$ in which $R^1, R^2, R^3$ and $R^4$, being the same or different, represents a moiety selected from the group consisting of —R, —OR, —COOR, and —SiR$^5$, R$^6$R$^7$ with R$^5$, R$^6$, and R$^7$ being identical or different, where each of R, R$^5$, R$^6$, and R$^7$ represent a hydrocarbyl radical containing 1 to 20 carbon atoms which is optionally substituted by at least one alkoxy group or at least one halogen.

6. A process for preparing a catalyst composition according to claim 1, comprising:
   (a) a step in which a rhenium compound is placed on the carrier;
   (b) a step in which drying is performed at a temperature of 0 to 250° C.;
   (c) an optional step in which thermal activation is performed by calcination in an oxidizing atmosphere at a temperature of 250° C. to 1000° C.;
   (d) a step in which a solid resulting from any of steps (a) to (c) is impregnated with a solution containing silicon;
   (e) an optional step in which drying of the solid from step (d) is performed at a temperature of 0 to 250° C.;

(f) a step in which thermal activation is performed by calcination in an oxidizing atmosphere at a temperature of 250° C. to 1000° C.

7. A process for preparing a catalyst composition according to claim 1, comprising:
(a) a step in which a solution containing silicon is impregnated on a porous mineral carrier;
(b) a step in which drying is performed at a temperature of 0 to 250° C.;
(c) an optional step in which thermal activation is performed by calcination in an oxidizing atmosphere at a temperature of 250° C. to 1000° C.;
(d) a step in which a rhenium, compound is introduced onto a solid resulting from any of steps (a) to (c);
(e) an optional step in which drying of the solid from step (d) is performed at a temperature of 0 to 250° C.;
(f) a step in which thermal activation is performed by calcination in an oxidizing atmosphere at a temperature of 250° C. to 1000° C.

8. A process for preparing a catalyst composition according to claim 1, comprising providing an existing carrier laden with rhenium oxide and conducting the following steps:
(a) a step in which a solution containing silicon is impregnated on a carrier laden with rhenium oxide;
(b) an optional step of drying at a temperature of 0 to 250° C.;
(c) a step of thermal activation by calcination in an oxidizing atmosphere at a temperature of 250° C. to 1000° C.

9. A catalyst composition according to claim 2, wherein the porous mineral carrier has a surface of 10 to 400 m²/g and a pore volume of at least 0.1 ml/g.

10. A catalyst composition according to claim 2, comprising rhenium in oxide form.

11. A catalyst composition according to claim 3, comprising rhenium in oxide form.

12. A catalyst composition according to claim 9, comprising rhenium in oxide form.

13. A catalyst composition according to claim 2, wherein the silicon compound is introduced in the form of a compound with Si—O bonds selected from the group consisting of ethyl tetraorthosilicate and compounds of general formula $R^1[R^3R^4SiO]_nR^2$ in which $R^1, R^2, R^3$ and $R^4$, being the same or different, represents a moiety selected from the group consisting of —R, —OR, —COOR, and —SiR$^5$, R$^6$R$^7$ with R$^5$, R$^6$, and R$^7$ being identical or different, where each of R, R$^5$, R$^6$, and R$^7$ represent a hydrocarbyl radical containing 1 to 20 carbon atoms which is optionally substituted by at least one alkoxy group or at least one halogen.

14. A catalyst composition according to claim 9, wherein the silicon compound is introduced in the form of a compound with Si—O bonds selected from the group consisting of ethyl tetraorthosilicate and compounds of general formula $R^1[R^3R^4SiO]_nR^2$ in which $R^1, R^2, R^3$ and $R^4$, being the same or different, represents a moiety selected from the group consisting of —R, —OR, —COOR, and —SiR$^5$, R$^6$R$^7$ with R$^5$, R$^6$, and R$^7$ being identical or different, where each of R, R$^5$, R$^6$, and R$^7$ represent a hydrocarbyl radical containing 1 to 20 carbon atoms which is optionally substituted by at least one alkoxy group or at least one halogen.

15. A catalyst composition according to claim 10, wherein the silicon compound is introduced in the form of a compound with Si—O bonds selected from the group consisting of ethyl tetraorthosilicate and compounds of general formula $R^1[R^3R^4SiO]_nR^2$ in which $R^1, R^2, R^3$ and $R^4$, being the same or different, represents a moiety selected from the group consisting of —R, —OR, —COOR, and —SiR$^5$, R$^6$R$^7$ with R$^5$, R$^6$, and R$^7$ being identical or different, where each of R, R$^5$, R$^6$, and R$^7$ represent a hydrocarbyl radical containing 1 to 20 carbon atoms which is optionally substituted by at least one alkoxy group or at least one halogen.

16. A catalyst composition according to claim 12, wherein the silicon compound is introduced in the form of a compound with Si—O bonds selected from the group consisting of ethyl tetraorthosilicate and compounds of general formula $R^1[R^3R^4SiO]_nR^2$ in which $R^1, R^2, R^3$ and $R^4$, being the same or different, represents a moiety selected from the group consisting of —R, —OR, —COOR, and —SiR$^5$, R$^6$R$^7$ with R$^5$, R$^6$, and R$^7$ being identical or different, where each of R, R$^5$, R$^6$, and R$^7$ represent a hydrocarbyl radical containing 1 to 20 carbon atoms which is optionally substituted by at least one alkoxy group or at least one halogen.

17. A process for preparing a catalyst composition according to claim 1, comprising providing an existing carrier laden with rhenium oxide and conducting the following steps:
(a) a step in which a solution containing silicon is impregnated on a carrier laden with rhenium oxide;
(b) an optional step of drying at a temperature of 0 to 250° C.;
(c) step of thermal activation by calcination in an oxidizing atmosphere at a temperature of 250° C. to 1000° C.

18. A catalyst composition according to claim 1, wherein the porous mineral carrier has a surface of 50 to 400 m²/g, and a pore volume of 0.3–1 ml/g.

19. A catalyst composition according to claim 1, wherein said composition comprises:
0.1 to 15% by weight of rhenium; and
0.05 to 5% by weight of silicon.

20. A catalyst composition according to claim 1, wherein said composition comprises:
0.5 to 10% by weight of rhenium; and
0.05 to 5% by weight of silicon.

21. A catalyst composition according to claim 5, wherein R, R$^5$, R$^6$, and R$^7$ are each an alkyl, cycloalkyl, alkenyl, aryl, aryl, or cycloalkyl radical containing up to 20 carbon atoms, which in each case is optionally substituted by at least one alkoxy group or at least one halogen.

22. A catalyst composition comprising at least one porous mineral carrier selected from among aluminas and silica-aluminas containing at least 75% by weight of alumina, said composition further comprising on said carrier
at least one rhenium, molybdenum, or tungsten compound, and
a silicon compound containing silicon in oxide form introduced onto the carrier in the form of ethyl tetraorthosilicate or a compound of general formula $R^1[R^3R^4SiO]_nR^2$ in which $R^1, R^2, R^3$ and $R^4$, being the same or different, represents a moiety selected from the group consisting of —R, —OR, —COOR, and —SiR$^5$, R$^6$R$^7$ with R$^5$, R$^6$, and R$^7$ being identical or different, where each of R, R$^5$, R$^6$, and R$^7$ represent a hydrocarbyl radical containing 1 to 20 carbon atoms which is optionally substituted by at least one alkoxy group or at least one halogen.

23. A catalyst composition according to claim 22, wherein said composition comprises:
0.01 to 20% by weight of rhenium, molybdenum, or tungsten in oxide form; and
0.01 to 10% by weight of silicon.

24. A catalyst composition according to claim 22, wherein the porous mineral carrier has a surface of 10 to 400 $m^2/g$ and a pore volume of at least 0.1 ml/g.

25. A process for preparing a catalyst composition according to claim 22, comprising:
(a) a step in which a rhenium, molybdenum, or tungsten compound is placed on the carrier;
(b) a step in which drying is performed at a temperature of 0 to 250° C.;
(c) an optional step in which thermal activation is performed by calcination in an oxidizing atmosphere at a temperature of 250° C. to 1000° C.;
(d) a step in which a solid resulting from any of steps (a) to (c) is impregnated with a solution containing silicon;
(e) an optional step in which drying of the solid from step (d) is performed at a temperature of 0 to 250° C.; and
(f) a step in which thermal activation is performed by calcination in an oxidizing atmosphere at a temperature of 250° C. to 1000° C.

26. A process for preparing a catalyst composition according to claim 22, comprising:
(a) a step in which a solution containing silicon is impregnated on a porous mineral carrier;
(b) a step in which drying is performed at a temperature of 0 to 250° C.;
(c) an optional step in which thermal activation is performed by calcination in an oxidizing atmosphere at a temperature of 250° C. to 1000° C.;
(d) a step in which a rhenium, molybdenum, or tungsten compound is introduced onto a solid resulting from any of steps (a) to (c);
(e) an optional step in which drying of the solid from step is performed at a temperature of 0 to 250° C.; and
(f) a step in which thermal activation is performed by calcination in an oxidizing atmosphere at a temperature of 250° C. to 1000° C.

27. A catalyst composition according to claim 22, wherein the porous mineral carrier has a surface of 50 to 400 $m^2/g$, and a pore volume of 0.3–1 mL/g.

28. A catalyst composition according to claim 22, wherein said composition comprises:
0.1 to 15% by weight of rhenium, molybdenum, or tungsten; and
0.05 to 5% by weight of silicon.

29. A catalyst composition according to claim 22, wherein said composition comprises:
0.5 to 10% by weight of rhenium, molybdenum, or tungsten; and
0.05 to 5% by weight of silicon.

30. A catalyst composition according to claim 22, wherein R, $R^5$, $R^6$, and $R^7$ are each an alkyl, cycloalkyl, alkenyl, aryl, aryl, or cycloalkyl radical containing up to 20 carbon atoms, which in each case is optionally substituted by at least one alkoxy group or at least one halogen.

* * * * *

UNITED STATES PATENT AND TRADEMARK OFFICE
CERTIFICATE OF CORRECTION

PATENT NO. : 6,908,878 B2  Page 1 of 1
DATED : June 21, 2005
INVENTOR(S) : Euzen et al.

It is certified that error appears in the above-identified patent and that said Letters Patent is hereby corrected as shown below:

Column 6,
Line 47, "$R^1,R^2,R^3$" should read -- $R^1$, $R^2$, $R^3$ --.
Line 49, "–R,–OR," should read -- –R, –OR, --.

Column 7,
Line 13, "rhenium, compound" should read -- rhenium compound --.
Lines 19 and 29, "of250°" should read -- of 250° --.
Lines 44 and 55, "$R^1,R^2,R^3$" should read -- $R^1$, $R^2$, $R^3$ --.
Line 66, "$R^1,R^2,R^3$" should read -- $R^1$, $R^2$, $R^3$ --.

Column 8,
Line 11 "$R^1,R^2,R^3$" should read -- $R^1$, $R^2$, $R^3$ --.
Line 41, "aryl, or cycloalkyl" should read -- or cycloalkyl --.
Line 53, "$R^1,R^2,R^3$" should read -- $R^1$, $R^2$, $R^3$ --.
Line 55, "–R,–OR," should read -- –R, –OR, --.

Column 10,
Line 4, "from step" should read -- from step (d) --.
Line 11, "mL/g" should read -- ml/g --.
Line 24, "aryl, or cycloalkyl" should read -- or cycloalkyl --.

Signed and Sealed this

Twenty-seventh Day of September, 2005

JON W. DUDAS
*Director of the United States Patent and Trademark Office*